US00PP09514P

United States Patent [19]

Taylor

[11] Patent Number: Plant 9,514

[45] Date of Patent: Apr. 23, 1996

[54] NECTARINE TREE 'PRINCE JIM'

[75] Inventor: James W. Taylor, Dinuba, Calif.

[73] Assignee: Ito Packing Company, Reedley, Calif.

[21] Appl. No.: 415,480

[22] Filed: Apr. 3, 1995

[51] Int. Cl.[6] ..... A01H 5/00

[52] U.S. Cl. ..... Plt./41.1

[58] Field of Search ..... Plt./41.1

[56] References Cited

U.S. PATENT DOCUMENTS

P.P. 6,471 12/1988 Taylor ..... Plt./41.1

P.P. 8,021 11/1992 Taylor ..... Plt./41.1

*Primary Examiner*—James R. Feyrer

*Attorney, Agent, or Firm*—Dennis B. Haase

[57] ABSTRACT

The tree of this invention, 'Prince Jim', is large, vigorous, spreading, open, vase formed, and regularly productive. Fruit formed is early, large for the early season, attractive, has fruit with a nearly totally red overcolor, yellow flesh irregularly striated with red and is clingstone. Fruit flesh is unusually firm at ripeness allowing for fruit in an advanced state of maturity to be harvested, shipped, and marketed for the fresh fruit market. As a result, fruit from this tree is distinctly sweeter than that from other, similar trees of similar market timing.

1 Drawing Sheet

BACKGROUND OF THE VARIETY

The present invention relates to a new and distinct variety of nectarine tree, which I refer to as 'Prince Jim' and having a yellow fleshed, cling stone fruit, which is particularly attractive in appearance, maturing in the early season period, which was developed from an ongoing fruit breeding program.

ORIGIN AND ASEXUAL REPRODUCTION OF THE NEW VARIETY

The novel nectarine was derived from an ongoing fruit breeding program for the improvement of nectarines to enhance quality and market acceptability. The flowers of the 'Big Jim' variety (U.S. Plant Pat. No. 8,021) were emasculated and pollenated with pollen from an early maturing variety obtained from earlier hybridizing work known in the program as 4K14A. Seeds produced by this method were stratified and grown to a height of about 18 inches. These seedlings were then bud grafted into dehorned 'Lovel' orchard trees in the experimental orchard of Ito Packing Co., Reedley, Calif. and tested under the variety number of 34L4.

SUMMARY OF THE VARIETY

The instant variety, developed through the above method, was particularly noticeable and eventually selected because of its deep red color, very firm flesh and good eating quality. The novel nectarine of the present invention has a much more attractive red color and larger size than other varieties ripening at the same period.

BRIEF DESCRIPTION OF THE DRAWINGS

The accompanying drawing illustrates typical specimens of the fruit and foliage of my new variety as grown in the San Joaquin Valley of California. Two views of a specimen are shown, one of which is a side elevation and the other an apex view. A third view is provided in side elevation and illustrating the internal texture and color of the flesh and pit.

DETAILED DESCRIPTION

The following is a detailed description of my new variety with color reference being to the *Maerz and Paul Dictionary of Colors,* except in the instance where terminology having general meaning is employed.

Parentage: 'King Jim'×Unnamed Selection F1.

Propagation: Maintains its distinguishing characteristics through several bud grafts.

Locality where grown and observed: Near Reedley, County of Fresno, Calif.

TREE

Size: Large, vigorous; spreading; open; vase form; productive, regular bearer.

Trunk: Medium size; medium texture.

Branches: Spreading.

Vigor: Vigorous, productive.

Regularity of bearing: Regular bearer.

Leaves:

*Color.*—Topside—31A10, underside 30A9.

*Size.*—17.6 mm. (7 inches) long and 4.5 mm. (1¾ inches) wide.

*Margin.*—Glandular; crenate.

*Petiole.*—Medium length; medium thickness.

*Glands.*—Average number— four; opposite; medium size; reniform; Position— usually two at the base of the leaf blade near the attachment of the petiole and occasionally one of the petiole near the leaf blade.

*Stipules.*—About 6 mm. (¼ inch) long at an early age.

Flower bud: Medium size.

Flowers: Large, showy.

Petals: Average size; 22 mm (⅞ inch) long and 16 mm (⅜ inch) wide. Some flowers may have three to four petaloids, as well as the regular five.

Color: Pink.

Date of full bloom: Approximately one week ahead of the variety 'Red Jim' (U.S. Plant Pat. No. 4,518); Feb. 17, 1995.

Anthers: Red.

FRUIT

Maturity:

*When described.*—First ripe, May 26, 1994.

Date of first picking: May 26, 1994.
Date of last picking: Jun. 8, 1994.
Size:
*Average axial length.*—7 cm. (2.75 inches); average transverse width in the suture plane—6.81 cm. (2.68 inches).
Form: Essentially round; may be slightly larger on either side of the ventral suture or or extended slightly on the side of the ventral suture.
Suture: Ventral suture is shallow but may deepen slightly toward the apex and extend slightly beyond the apex and extend toward the dorsal side. The dorsal suture is very shallow except near the apex where it may deepen to meet the ventral suture.
Ventral surface: Smooth.
*Cavity.*—Round, deep (average depth ⅝ inches) with small area of stem attachment.
*Base.*—Flattened slightly.
*Apex.*—Recessed in the suture usually, but on certain fruit it can be extended to beyond the suture. Apparently, depending on climatic and other orchard conditions more slightly extended sutures may be found. The apex may be slightly curved on some fruits.
*Skin.*—Medium thick; medium texture.
*Tendency to crack.*—None observed.
*Bloom.*—Wanting.
*Color.*—Yellow (9L5) only around the base and in the early stages of maturity in most fruit. When fruit becomes tree ripe the under color becomes a deep orange (3I11), increasing to a deeper red orange (4K11) with increasing maturity. At maturity the over color is a bright red (7L8) darkening to a deep red (5L11).
Flesh:
*Texture.*—Very firm. Even in the very mature condition when taste quality is maximum, the flesh is firm enough to withstand picking and packing pressures without bruising.
*Color.*—Yellow (10K2), changing to a light orange color as the fruit matures, especially around the periphery. Scattered areas, especially around the apex and fibres, deepen with increasing maturity to red (2H5).
*Flavor.*—Good balance of acid and sugar.
*Juice.*—Abundant.
*Aroma.*—Not very pronounced.
*Fibres.*—Sparsely running through the flesh, but less obvious than many nectarines.
*Ripening.*—Even, stays firm on the tree for a long time as it matures.
*Eating quality.*—Excellent.
Stone:
*Adherence to the flesh.*—Cling stone.
*Size.*—Average thickness 1.9 cm. (¾ inch); average width 2.54 cm. (1 inch); average length 2.9 cm. (1⅛ inches).
*Form.*—Oval.
*Apex.*—Sharply pointed in most.
*Hilum.*—Small, oblong.
*Dorsal edge.*—Shallow grooves.
*Ventral edge.*—Narrow, very little wing toward the apex.
*Surface.*—Irregularly pitted with deeper grooves toward the base.
*Color.*—Light redish brown (3D8).
Use: Fresh market.
Keeping quality: Excellent.
Resistance of disease: Similar to other glanded varieties of nectarine varieties.

Althought this novel variety of nectarine possesses the described characteristics as a reuslt of the growing conditions in the Reedley area of Fresno County, Calif., in the central portion of the San Joaquin Valley, it is to be understood that variations of the usual magnitude in characteristic incident to the growing conditions, fertilization, pruning and pest control are to be expected.

Having thus described and illustrated my new nectarine tree, what is claimed as new and desired to be secured by Letters Patent is:

1. A new and distinct variety of nectarine tree, substantially as herein shown and described, with fruit of yellow flesh around the base in early stages of maturity, being cling stone type, with tree ripe fruit having an under color of deep orange and increasing to deeper red orange with increasing maturity, having a maturity period in the early part of the season with good eating quality, bearing fruit of much larger size than other varieties at this season and being much firmer than fruit of other varieties so it can be harvested at a very mature stage.

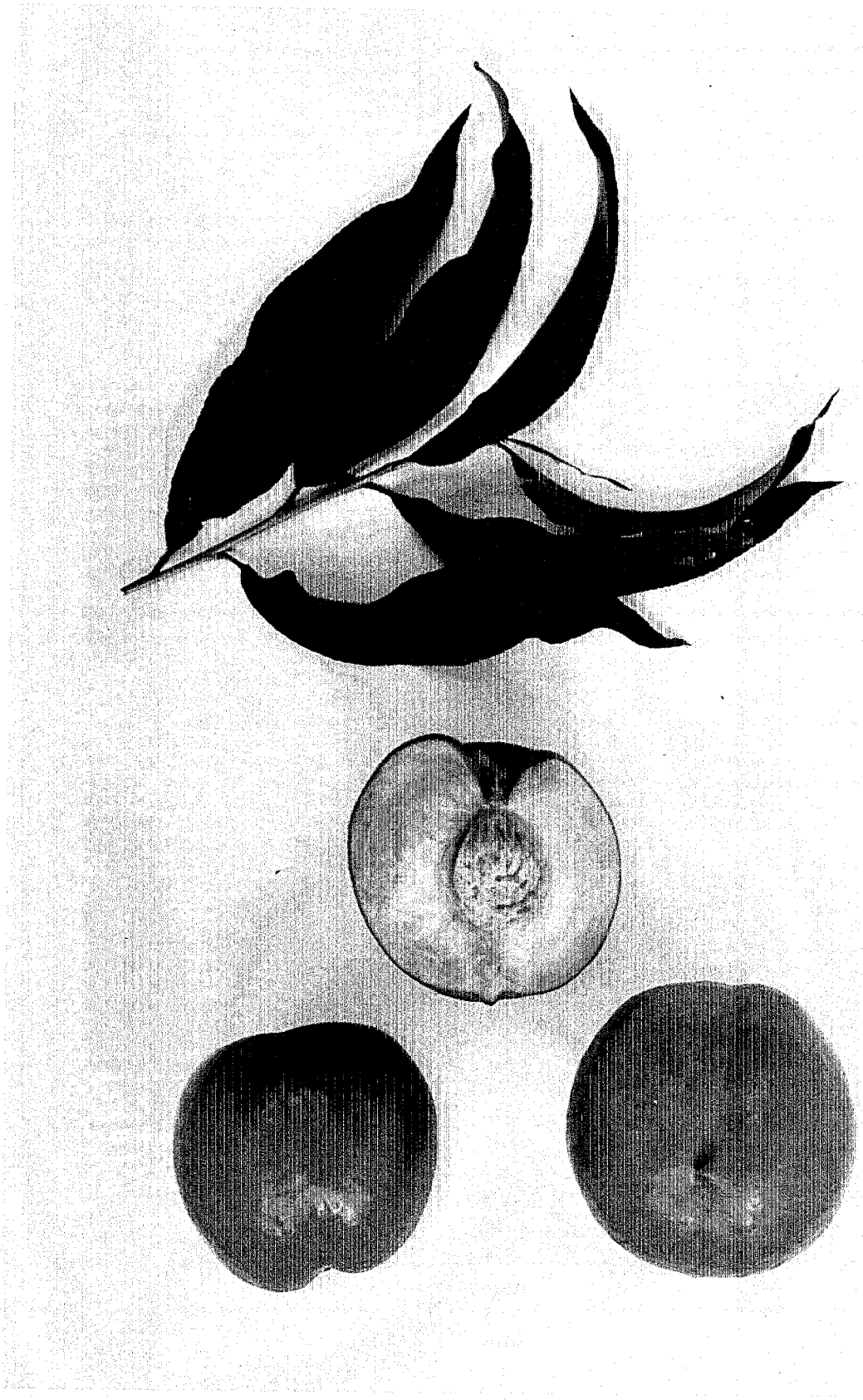

* * * * *